United States Patent [19]

Hayes et al.

[11] Patent Number: 5,403,863
[45] Date of Patent: Apr. 4, 1995

[54] SCOLYTID REPELLANT

[75] Inventors: Jane L. Hayes; Brian L. Strom, both of Pineville; Lawrence Roton, Pollock, all of La.; Leonard Ingram, Jr., Starkville, Miss.

[73] Assignees: The United States of America as represented by the Secretary of Agriculture, Washington, D.C.; Mississippi State University, Forest Products Lab, Mississippi State, Miss.

[21] Appl. No.: 113,709

[22] Filed: Aug. 31, 1993

[51] Int. Cl.⁶ ............... A01N 31/14; A01N 25/00; A01N 25/08
[52] U.S. Cl. ................... 514/717; 514/919; 424/405; 424/409
[58] Field of Search ............... 514/717, 719; 424/405, 424/409, 84

[56] References Cited

U.S. PATENT DOCUMENTS

| 4,880,624 | 11/1989 | Metcalf et al. | 424/84 |
| 5,273,996 | 12/1993 | Dickens et al. | 514/919 |
| 5,281,418 | 1/1994 | Lindgren et al. | 514/919 |

OTHER PUBLICATIONS

Werner, Richard A. "Response of the Beetle, *Ips grandicollis*, to Combinations of Host and Insect Produced Attractants" J. Insect. Physiol., 1972, vol. 18, pp. 1403–1412.

*Primary Examiner*—Allen J. Robinson
*Assistant Examiner*—John D. Pak
*Attorney, Agent, or Firm*—Oblon, Spivak, McClelland, Maier & Neustadt

[57] ABSTRACT 4-allylanisole is demonstrated to be an effective repellant for scolytid infestation. Conifers, a particular target for the scolytids, are protected by application of 4-allylanisole, either directly or suspended in a carrier, in concentrations as low as 0.01 percent. The repellant can be administered in conjunction with other repellants and insecticides.

7 Claims, 3 Drawing Sheets

SCOLYTID REPELLANT

BACKGROUND OF THE INVENTION

1. Field of the Invention

This invention pertains to a repellant for the well-documented insect pests of the beetle family Scolytidae. Specifically, 4-allylanisole, a component of the resin of the preferred target of the scolytids, Pinus, and other conifers, has been identified as a repellant for the southern pine beetle (SPB), *Dendroctonus frontalis* Zimm., and related scolytid pests. This repellant can be used to protect potential host trees from attack by scolytids.

2. Background of the Prior Art

Infestation of conifers by scolytids has been well documented. Considerable attention has been devoted to protection of high-value stands, as well as single trees, threatened by SPB and other scolytids for the preservation of wildlife, cultural and recreational resources. This focused attention on biorational tactics has been largely devoted to efforts using synthetic semiochemicals, in particular, the insects own anti-aggregation or inhibitor pheromones such as verbenone, Payne et al, *Journal of Applied Entomology*, 114:341–347 (1992).

There has also been substantial attention devoted to analysis of the method and sequence of attack by the SPB and other scolytids on the target trees. While the process of selection is not well understood, it appears that "pioneer" insects (e.g., females in Dendroctonus spp. and males in Ips spp.) initiate the attack on susceptible host trees, and conspecifics follow in response to attractant pheromones such as frontalin. Secondary pheromones, including inhibitory pheromones, are also involved.

The trees respond to this attack by secreting resins. The resins secreted have been the subject of a variety of studies. Numerous chemicals have been identified in the resin, one of which is 4-allylanisole, also known by a variety of chemical synonyms, including estragol(e), methyl chavicol, methoxyallylbenzene and tarragon. The presence of this phenylpropanoid compound has been identified among a wide variety of terpenes and resin acids.

4-allylanisole was targeted as a potential inhibitor of fungal growth, of which growth is believed necessary for successful SPB infestation. Bridges, *Phytopathology*, 77:83–85; January, 1987. The Bridges reference speculates with respect to the impact of 4-allylanisole on the SPB but provides no data and does not suggest repellant activity.

Other researchers have focused on the action of other terpenes in the pine resin, and while noting the presence of 4-allylanisole, have not ascribed to any particular activity with respect to the various bark beetles targeted. Representative articles include Renwick et al., "Systems of Chemical Communication in Dendroctonus", *Contributions from Boyce Thompson Institute*, 24:283–292, 1970.; Werner, *Journal of insect Physiology*, 18:423–438, 1972; Pierce et al., *Journal of Chemical Ecology*, 13:1525–1542, June, 1987; Salom et al., *Journal of Chemical Ecology*, 17:2527–2538, December, 1991; and Salom et al., *Journal of Applied Entomology*, 114:472–479, 1992. Of these references and studies, Werner is perhaps the most complete. The Werner article concludes that 4-allylanisole, therein identified as methyl chavicol, is an attractant for the *Ips grandicollis*, stimulating, after purification, a 90 percent response rate at a 1.0 percent concentration value among male beetles and a 50 percent response rate among female beetles.

Current measures for protecting loblolly pine and other potential host trees from scolytid infestation remain inadequate. Although three compounds (chloropyrifos, fenitrothion, carbaryl) in addition to lindane are now registered for use against bark beetles, increased federal restrictions may curtail their use in the future. These traditional chemical insecticides can be used to protect high value trees (Amman, "Integrated Control of the Mountain Pine Beetle in Lodgepole Pine Forests", *Proc XVI, IUFRO World Congr. Norway*, pp 439–446, 1976), although carbaryl is not effective against SPB (Berisford et al., "Efficacy Studies: Prevention", *USDA Forest Serv. Gen Tech Report SE-21*, pp 3–8, 1981). However, the high cost of labor and the products, and the need to spray all surfaces of the bole for effective control will always restrict the use of topically applied chemicals (Billings, "The Southern Pine Beetle", Chapter 10, *USDA Agrig. ESPBRAP, For. Serv., SEA. Tech. Bull. No.* 1631, 1980). In addition, relying solely on chemical sprays, especially the use of only one or a few, increases the risk of development of resistance in the pest population (Pimentel et al., "Effects of Single Versus Combinations of Insecticides on the Development of Resistance", *Environ. Entomol.* 14:582–589, 1985). Other inherent detrimental effects are associated with the use of these insecticides. Their use reduces the quality of the environment, and alters the ecosystem by reducing species diversity, modifying the food chain, and altering patterns of energy flow and nutrient cycling (Pimentel et al., "Pesticides and Ecosystems", *BioScience* 32(7):595–600, 1982). Many of these effects can persist for long periods. For example, lindane can be very persistent in the environment (residues remaining on logs one year after treatment and washed in water for 2 hours still exceed the tolerance threshold of fish) (Austra, "Lindane Residues on the Bark of Sprayed Logs", *Norwegian For. Res. Instit. Report* 3184, 8 pp, 1984). Insecticides may adversely affect natural enemies. All of these registered chemicals have serious impacts on natural enemies and soil arthropods (e.g., [Williamson et al , "Impact of Insecticidal Control on the Southern Pine Beetle Population in East Texas, *J. Econ. Entomol.* 64:1140–1144, 1971]; [Carter et al., "Seasonal Abundance of Certain Soil Arthropods in a Fenitrothion-Treated Red Spruce Stand", *Can. Entomol.* 105:1065–1073, 1973]; [Hoy et al., "Effects of Lindane, Chlorpyrifos and Carbaryl on a California Pine Forest Soil Arthropod Community", *Environ. Entomol.* 10:732–740, 1981]; [Swezey et al , "Comparative Toxicity of Lindane, Carbaryl, and Chloropyrifos to Western Pine Beetle (*Dendroctonus brevicomis*) (Coleoptera: Scolytidae) and Two of its Predators, *Enoclerus iecontei* (Coleoptera: Cleridae) and *Temnochila chlorodia* (Coleoptera: Trogostidae)", *Can. Entomol.* 114:397–401, 1982]; and [Werner et al., "Laboratory and Field Evaluation of Insecticides Against The Spruce Beetle (Coleoptera: Scolytidae) and Parasites and Predators in Alaska", *J. Econ. Entomol.* 76:1144–1147, 1983]). The most widely used semiochemical, verbenone, an anti-aggregation pheromone, fails to inhibit a large number of attacks and has little or no effect on female SPB (Salom et al., "Effect of Verbenone Enantiomers and Racemic endo-Brevicomin on Response of *Dendroctonus frontalis* (Coleoptera: Scolytidae) to attractant-baited traps", *Can. J. For. Res.* 22:925–931, 1992).

Accordingly, it remains a goal of those skilled in the art to establish a more effective means of protecting loblolly pines and other conifers from attack by SPB and related pests, preferably without the introduction of a chemical foreign to the established parameters of the infestation process.

SUMMARY OF THE INVENTION

The applicants have now discovered that 4-allylanisole is in fact an effective repellant for the SPB and related scolytid pests, over a wide range of concentrations. The repellant is at least as effective as the dominant experimental product available, verbenone, and affects adult beetles of both sexes, whereas verbenone is male-biased (not the pioneering sex in Dendroctonus), 4-allylanisole is commercially available, and a chemical naturally incorporated in the resin of trees subject to bark beetle infestation. Accordingly, it offers a desirable means of protecting important natural resources.

The 4-allylanisole can be applied directly to the potential targets of scolytid infestation, neat or as a concentrated liquid, or as a vapor, or in a liquid, vapor, or powdered carrier. The effective concentration will vary with the conditions presented, and repeated application of the protectant may be necessary as environmental action, including rain and wind, carry off or degrade the chemical repellant. The repellant has been demonstrated in repeated tests to yield substantial protection, both in the laboratory, and in controlled field tests.

DETAILED DESCRIPTION OF THE INVENTION

Figure 1:
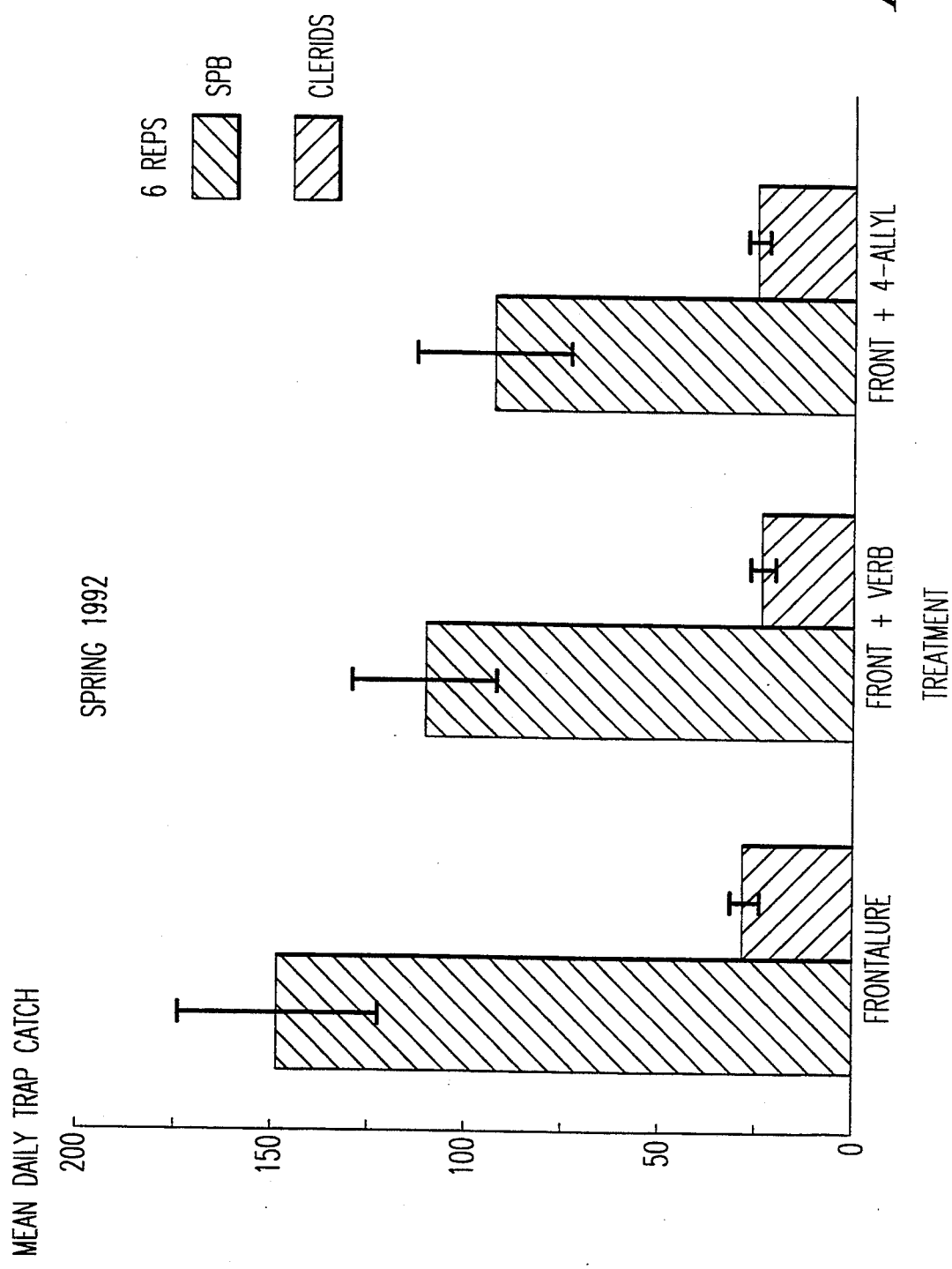
FIG. 1 is a graph reflecting the relative capture rate of traps baited with FRONTALURE alone (SPB aggregation pheromone + the synergist alpha pinene), as a control, as opposed to traps baited with FRONTALURE and verbenone or FRONTALURE and 4-allyanisole conducted during the Spring.

In order to protect the hosts of scolytid pests, such as loblolly pine and related trees subject to attack by SPB and related scolytids (related possible tree hosts include all yellow pines (eastern and western species), the white pines (eastern and western species), Norway spruce, larch spp., eastern red cedar, eastern hemlock, Fraser fir and Douglas fir), the 4-allylanisole insect repellant is applied to individual trees. 4-allylanisole has been previously isolated, and is commercially available. The compound is most frequently commercially identified as estragol(e), and may be obtained from a variety of manufacturers, including Aldrich, Lancaster, Berje, Penta, and Pfaltz and Bauer. The repellant, neat or when admixed with a carrier, can be applied in liquid form to the bark of the tree, by application of solid supports, such as wicks and polymer masses impregnated with the compound and other elution devices known to those skilled in the art, and by application of sprays and powders to the trees, particularly for wide-range application. A minimum effective concentration of the 4-allylanisole is believed to be 0.01 percent, but greater concentrations, on up to 100 percent can be employed.

The preparation of diluted repellant compositions will not be detailed herein. Suffice it to say that conventional carriers used for the preparation of insecticides and insect repellants known to those of skill in the art can be used in conjunction with the 4-allylanisole repellant, as is currently practiced in the industry.

Because the invention is a repellant rather than an insecticide, broadcast dispersal is unlikely to be effective. Application from pressure sprayers directly to potential hosts, or eluted from solid supports (as mentioned), however, offer reasonable facile and effective means for protecting these important natural resources.

To demonstrate the effectiveness of the repellant, 4-allylanisole was tested in laboratory trials, as well as limited field trials. These trials are described herein below, and then summarized in tabular form in the tables following. These examples are not to be interpreted as limiting, but merely reflect the effectiveness of 4-allylanisole, both in the abstract, and as compared with the experimental dominant inhibitor, verbenone.

EXAMPLES

Laboratory Assay:

To test individual beetle response to 4-allylanisole versus verbenone a simple assay was devised. A strip (5 mm wide) of 4-allylanisole (Aldrich Chemical Co., Inc., Milwaukee, Wis.) or verbenone (34% + :66% — Borregaard, Inc.) was "painted" with a camel's-hair brush in a circle (~17 cm diam) on a piece of cardboard (28 × 12.5 cm). After 3 min, beetles (2–5 individuals) were released in the center of the treated circle. Responses ($\leq 30$ s exposure) were recorded as not- repelled or repelled; scored beetles were then placed in separate containers by response and later sexed.

A beetle was designated not-repelled if it walked through the treated circle or stopped but proceeded across the circle within 30 s of exposure. A beetle was designated repelled if it moved toward the circle but stopped abruptly and raised antennae (some "rear-up" on hind legs), stood motionless, and/or moved away from the circle (some move abruptly in the opposite direction).

Testing was conducted at room temperature (22°–25° C.) with light supplied from an adjoining room. An object was used to cast a shadow over the test circle (<10 ft candles). Beetles were refrigerated briefly before testing to reduce their tendency to fly. Only beetles that were capable of walking up the sides of a collection container were used for this experiment. In each trial and for each compound, 50 apparently healthy beetles were selected at random and tested. Another 50 beetles were then selected and tested with the other compound. The order of compound use was also random.

Trials were conducted with:

1. Newly emerged *D. frontalis* in three trials (n=50 beetles per compound per trial) were collected on three different dates from the same source population (Colfax, La.). Beetles were obtained from two infested loblolly pines (ca. 24 cm dbh) which were felled with brood in the pupa or callow adult stage. Four bolts (45 cm long) were cut from each tree and placed in two separate (by tree) rearing cans to collect adults as they emerged. Assays were conducted on the day of emergence; beetles tested on 12 Mar. 1992 originated from the same tree and those test on 2 April and 3 April originated from the second tree.

2. Newly emerged and re-emerged *D. frontalis* from the same generation and source population were used (Colfax, La.). Newly emerged beetles (n=100) were obtained, as described above, from an infested loblolly at the front of an active infestation with brood in the callow adult stage. A nearby freshly attacked tree was felled in order to obtain parent adults (n=100) re-emerging ~20 days later. Bolts from each tree were placed in rearing cans for collection.

3. Trials were also conducted with a clerid beetle, *Thanasimus dubius* (Say) and five other scolytid species. *T. dubius* (n=50) for this study were obtained over a three-day period from five traps baited with *D. frontalis* aggregation pheromone (frontalin+turpentine) (Catahoula, R.I.). Newly emerged engraver beetles, *Ips avulsus* (Eichhoff) (n=50) and *I. calligraphus* (Germar) (n=9), typical associates of *D. frontalis* were obtained from bolts from a single loblolly tree from an infestation containing both *D. frontalis* and *Ips*, which were held in rearing cans. Mountain pine beetle (n=50), *Dendroctonus ponderosae* Hopkins, a univoltine western species were extracted prior to emergence from bolts of lodgepole pines from a site (~16 km north of LaPine, Oreg.) in central Oregon and mailed overnight on ice to the Alexandria Forestry Center (AFC), Pineville, La. for testing. Similarly, western pine beetle (n=50), *D. brevicomis* LeConte, another western species ecologically similar to *D. frontalis* were extracted prior to emergence from ponderosa pine bolts from a site (MiWuk Village, Calif.) in the Sierra foothills of California. These insects were sexed and then mailed overnight on ice to AFC for testing. Newly emerged *Ips pini* (Say), a transcontinental northern species, were obtained from a laboratory colony maintained on red pine (*Pinus resinosa*), housed at the University of Wisconsin, which was originated from Sauk Co, Wis. and replenished annually; specimens were mailed overnight to AFC. In all cases only apparently healthy beetles were used.

Field Assay:

A test of local beetle populations response to 4-allylanisole and verbenone (vs the attractancy of frontalure) was conducted using baited multiple-funnel (16 funnel) traps (Lindgren 1983). Traps were placed in active *D. frontalis* infestations in the spring (April–June) (6 replicates in 6 sites) and fall (Sept) (7 replicates in 4 sites); The treatments (2 traps per treatment) consisted of FRONTALURE ® [*D. frontalis* aggregation pheromone frontalin (BASF, Limberhoff, F.R.G.+a-pinene (Aldrich, Inc., Milwaukee, Wis.) (1:2)], FRONTALURE+verbenone, and FRONTALURE+4-allylanisole. Traps were placed no less than 10 m from each other, from green trees, or from infested trees with emerging brood. Placement of treatments was initially randomly assigned and then changed daily in a sequential order for six days. In the spring replications, baits were moved daily among stationary traps, whereas in the fall whole traps with baits were moved. Collection cups contained a 5.5 by 2 cm piece of peststrip (2,2 dichlorovinyldimethylphospate, Loveland Industries, Inc.). The number of *D. frontalis* and *T. dubius* were collected and recorded daily.

Bait preparation differed slightly between seasons Spring—FRONTALURE ® (~3.5 ml) was eluted from a single polyethylene transfer pipette (Samco ®, St.-Amand Mfg. Co, Inc., San Fernando, Calif.); verbenone (5 ml; −66%:+34%) was eluted from a 2.5×1.75×0.375 cm cellulose sponge in a 0.7 mil white plastic bag (low density polyenthylene, United Plastic Films, Inc., Carterville, Ga.); and 4-allylanisole (5 ml) was prepared as verbenone. Fall—FRONTALURE was unchanged; verbenone (10 ml) was eluted from a bag (prepared by FPM); and in four sites 4-allylanisole was eluted from a 20 ml polyethylene vial with cotton wick in one trial followed by a second trial in three of the four sites using the bag devise used in the spring replicates. Elution rates were determined gravimetrically at 24 h intervals under typical field conditions in the Spring and in the laboratory during the Fall.

To determine if there was a difference between sexes in response to the various baits, sex ratios were obtained from one spring replicate (GT1) based on subsampling up to 50 *D. frontalis* per trap from daily collections. Similarly, as part of another study, sex ratios were obtained for *D. frontalis* trapped per day in an assay conducted from 3–9 Jul. 1993 in an active infestation on the Catahoula R.I. (#CA3034). In this test, traps were baited with FRONTALURE alone and simultaneously with verbenone, 4-allylanisole, limonene, or 4-allylanisole+limonene These data were analyzed for fit to 1:1 by chi square and contingency table analysis (Statistix 4.0, Analytical Software 1992).

Dose-response experiments were conducted to test:

1. Response to FRONTALURE given increasing number of 4-allylanisole elution devices (five replicates, May–Oct 1992). Traps were baited (two traps per treatment) with FRONTALURE alone or FRONTALURE+one, two, or four 4-allylanisole elution devices. Treatment position was initially randomly assigned and then changed daily in a sequential order for five to eight days.

2. Response was tested to frontalin given an increasing percentage of 4-allylanisole when mixed with turpentine (one replicate, one site. Each trap was baited with one pipette containing frontalin and one with either 100% turpentine, 75% turpentine and 25% 4-allylanisole, 50% turpentine and 50% 4-allylanisole, 25% turpentine and 75% 4-allylanisole, or 100% 4-allylanisole. In both dose-response experiments the number of *D. frontalis* and *T. dubius* were recorded daily as described above.

In a single trial, response of *D. frontalis* to 4-allylanisole in combination with verbenone was tested. Treatments (two traps per treatment) consisted of FRONTALURE alone, FRONTALURE+4-allylanisole (two wicked 20 ml vials), FRONTALURE+verbenone (two 10 ml bags), and FRONTALURE+4-allylanisole (one vial)+verbenone (one bag).

Data Analysis

In all field assays, mean values of *D. frontalis* and *T. dubius* were tested for normality, ln+1 transformed, and analyzed by ANOVA (PROC GLM, SAS Institute 1988). Separation of the transformed means was performed by LSMeans. Dose response test data were analyzed by ANOVA and regression analysis (PROC GLM and PROC REG, SAS Institute 1988). Mean values for dose response data were transformed as ln (x+0.001) and separation of the transformed means was performed by LSMeans.

Preliminary field trials:

A loblolly pine (*Pinus taeda* L.), struck by lightning on 1 Jun. 1992, was treated with 4-allylanisole on 3 Jun. 1992. A longleaf pine (*P. palustris* Mill.), struck by lightning on 1 July was treated with 4-allylanisole on 2 Jul. 1992. The treatment consisted of placing nine 20 ml polyethylene vials with cotton wicks, evenly spaced from the ground to 8 m up the tree bole on the damaged side. A loblolly and longleaf struck by lightning in the same storms were located the same day and served as controls. At day 30, numbers of *D. frontalis* attacks were counted in a 15.2 cm wide band and around the tree circumference at 2 and 4 m up the bole.

RESULTS

Laboratory Assay:

Male and female *D. frontalis*, newly emerged and to a lesser extent re-emerged, were repelled when exposed to 4- allylanisole in laboratory assays. Generally, beetles that were "repelled" by 4-allylanisole demonstrated a higher degree of alarm and more abrupt behavior than beetles "repelled" by verbenone. Although the percentage varied from trial to trial, higher percentages of *D. frontalis* in all trials were repelled by 4-allylanisole than verbenone using the same assay method. In trial 1, regardless of sex, 84% of the newly emerged beetles exposed to 4-allylanisole were repelled, while 11% of those exposed to verbenone were repelled. In trial 2, regardless of sex, higher percentages of the newly or re-emerged beetles exposed to 4-allylanisole were repelled than those exposed to verbenone (46 and 52% higher, respectively). In both treatments fewer re-emerged beetles were repelled (32% less for 4-allylanisole and 38% less for verbenone).

The *D. frontalis* predator, *T. dubius*, showed no repellent response when exposed to 4-allylanisole or verbenone in laboratory assays. Other scolytids tested, including local (*I. avulsus* and *I. calligraphis*) and non-resident species (*I. pini*, *D. brevicomis*, and *D. ponderosae*), were also repelled when exposed to 4-allylanisole in laboratory assays; equal or higher percentages were repelled by 4-allylanisole than verbenone.

Field Assay:

Significantly fewer *D. frontalis*, in the spring and fall, were captured in traps baited with 4-allylanisole+FRONTALURE than FRONTALURE alone; trap captures differed between 4-allylanisole- and verbenone-baited traps in the spring but not in the fall trials. No trial by treatment interaction was found with analysis of variance in either spring or fall trials (F=0.36; df=5,2; P<0.9614 and F=0.19; df=5,2; P<0.9984, respectively). However, that trap captures vary day to day, presumably influenced by weather conditions, is evident in significant results of a model in which day is treated as a nested component of trial. *T. dubius* attraction was apparently unaffected by the addition of 4-allylanisole; however, in the spring trials significantly fewer *T. dubius* were captured in traps baited with verbenone+FRONTALURE than 4-allylanisole+ or FRONTALURE alone. Based on mean captures in FRONTALURE alone traps, both *D. frontalis* and *T. dubius* showed seasonal differences in abundance, with significantly more *D. frontalis* captured in the fall than in the spring (245.4±40.3 vs 149.9±25.6), in contrast significantly more *T. dubius* were captured in spring than in the fall (28.5±3.2 vs 4.8±0.6).

In Spring trials (FIG. 1), 4-allylanisole-baited traps captured significantly fewer *D. frontalis* than traps baited with FRONTALURE alone or verbenone (P<0.0001 and P<0.0004, respectively, LSMean, SAS Institute 1988). The mean number of *D. frontalis* captured in FRONTALURE alone and verbenone-baited traps did not differ (P<0.2179). *T. dubius* captures did not differ significantly between traps baited with 4-allylanisole and FRONTALURE alone, but both captured significantly more *T. dubius* than verbenone-baited traps (P<0.0391 and P<0.0231, respectively).

Figure 2:
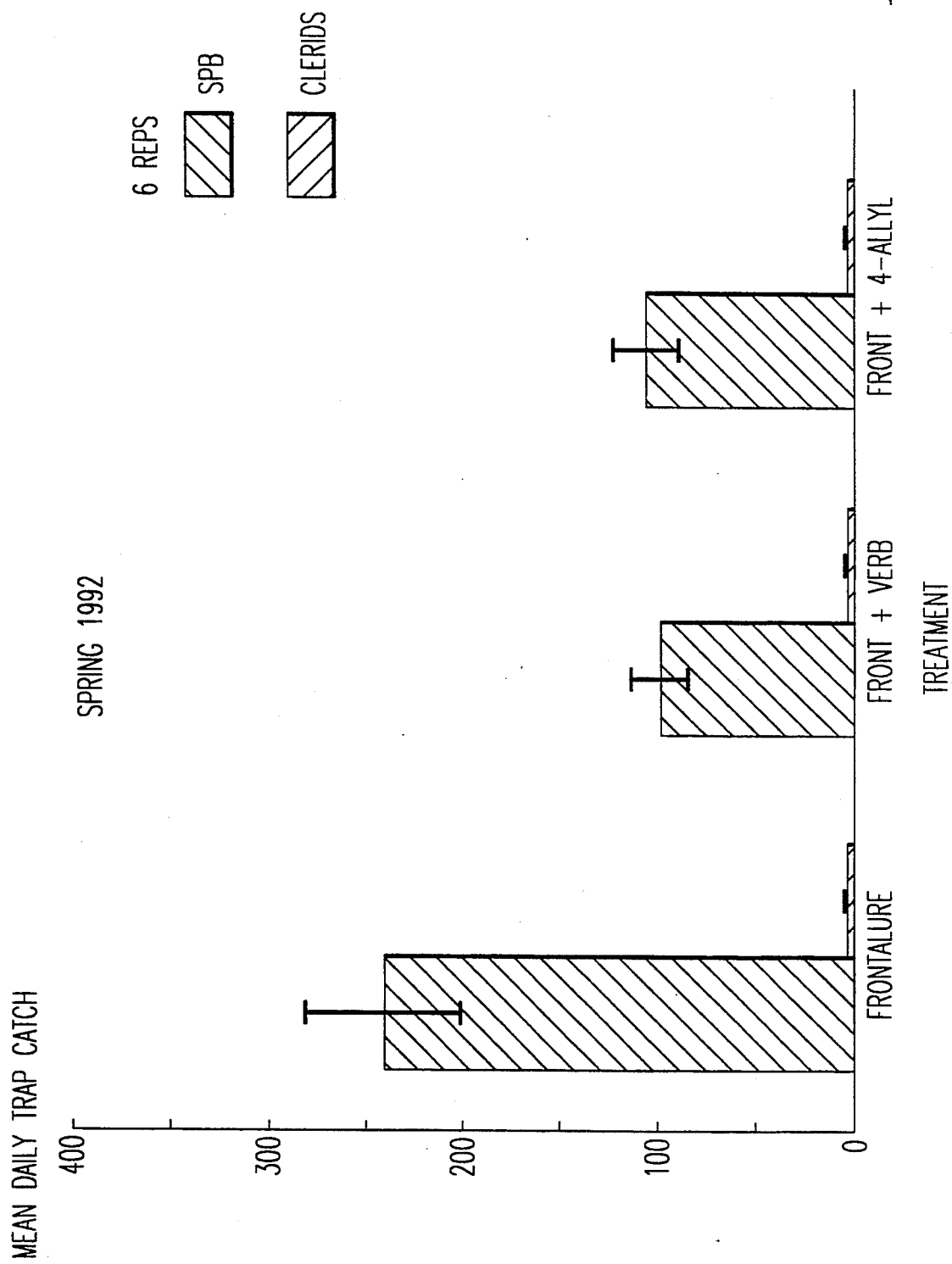
FIG. 2 is a graph comparing capture rates for traps baited in the fashion described for FIG. 1, but conducted in the Fall.

In Fall trials (FIG. 2), verbenone and 4-allylanisole-baited traps captured significantly fewer *D. frontalis* than traps baited with FRONTALURE alone (P<0.0001, LSMeans, SAS Institute 1988). There were no differences between *D. frontalis* captured in 4-allylanisole- and verbenone-baited traps. *T. dubius* captures did not differ significantly among treatments.

Sex ratios of *D. frontalis* captured in traps baited with aggregation pheromone alone were on average significantly male-biased (57% GT1 and 74% CA3034) as has been previously reported (e.g., Kinzer et al. 1969, Payne et al. 1978). The mean sex ratio (55% male GT1 and 71% CA3034) for *D. frontalis* captured in traps with FRONTALURE+4-allylanisole did not differ significantly from FRONTALURE alone, whereas captures in traps baited with FRONTALURE+verbenone differed significantly in sex ratio from FRONTALURE alone (Pearson's chi=102.46, P<0.0001 GT1; chi=23.94, P<0.0001 CA3034). A significant female bias (66% female; chi sq=33.06, P<0.0236) was observed in verbenone-baited traps at GT1 and a slight but not significant female bias was observed at CA3034 (52% female). A similar biased response was also apparent in trapping results presented by Salom et al. (1993).

In a single trial in which 4-allylanisole, verbenone, and the combination were added to FRONTALURE-baited traps, all three captured significantly fewer *D. frontalis* than FRONTALURE alone but did not differ from each other (P<0.0004; P<0.0011; P<0.0016; LSMeans, respectively). In rank order, 4-allylanisole caught the least (16.75±4.02; mean±SEM) followed by 4-allylanisole+verbenone (19.19±4.37), verbenone (21.19±5.95), and FRONTALURE alone (45.88±11.02). The mean number of *T. dubius* captured did not differ among treatments.

Figure 3:
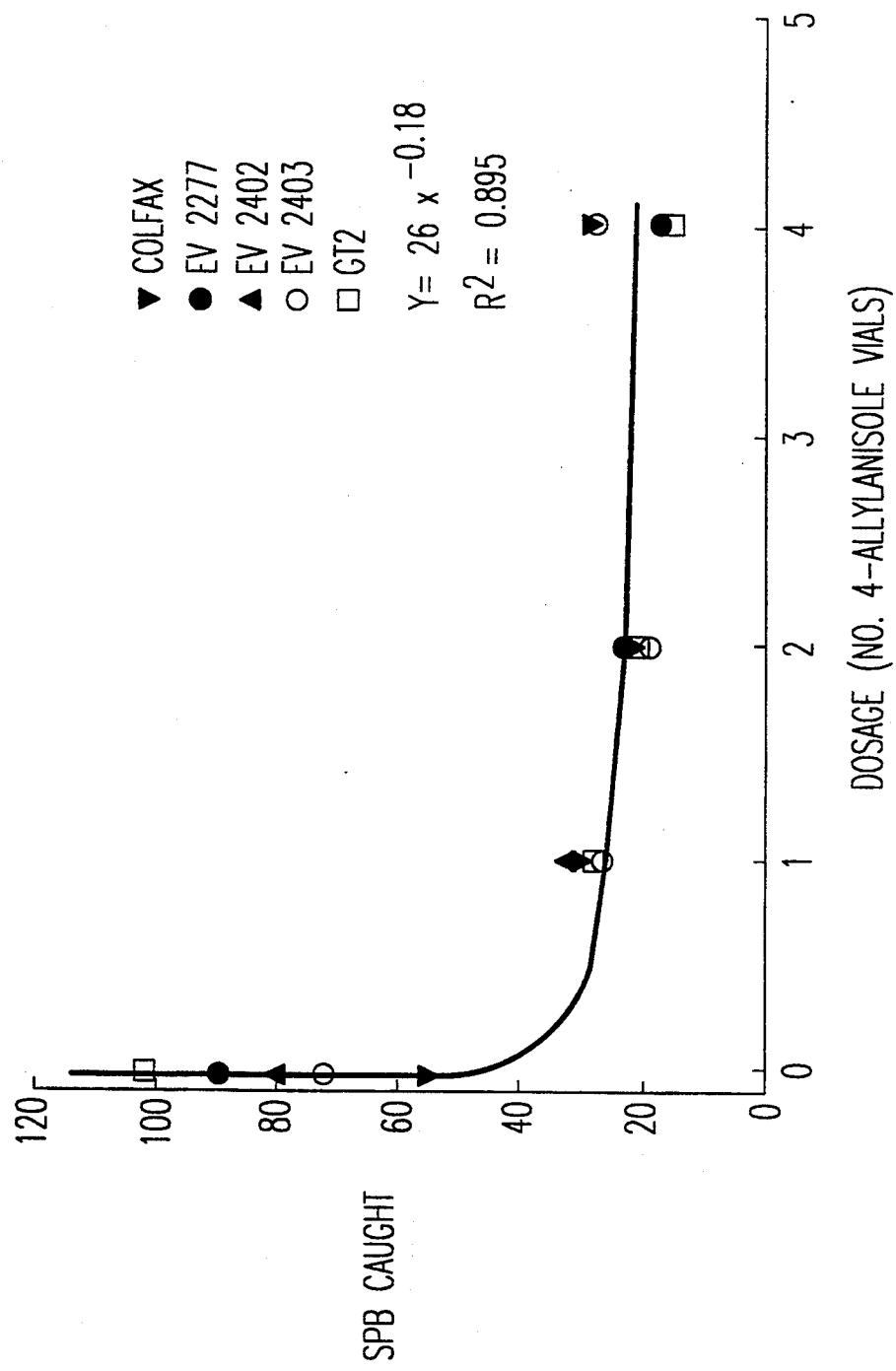
FIG. 3 graphically illustrates the impact of enhanced dosage of 4-allyanisole on repellant effect.

The repellent effect of 4-allylanisole on *D. frontalis* is not significantly enhanced by the addition of more than one wicked elution device with 20 ml 4-allylanisole, dose-response of *D. frontalis* is defined by $Y = 26 X^{-0.16}$ ($R^2 = 0.895$; n=5; P<0.0001) (FIG. 3). Frontalure-baited traps captured significantly more *D. frontalis* than traps baited with FRONTALURE+one, two or four 4-allylanisole elution devices (x=79.8±7.98, P<0.0001, LSMeans, SAS Institute 1988). However, there were no differences in mean captures between the different number of devices (x±SEM=29.4±0.87; 21.6±0.75; 20.8±2.76). The addition of one or more 4-allylanisole elution devices did not impact *T. dubius* attraction to FRONTALURE (10.9±0.98, 9.8±0.80, 11.3±0.89); however, all three captured significantly fewer clerids than frontalure alone (17.6±1.61, P<0.01 LSMean, SAS Institute 1988).

Differing ratios of turpentine:4-allylanisole, above 25% 4-allylanisole, did not significantly influence the repellent effect of 4-allylanisole on *D. frontalis*. Traps baited (in separate elution devices) with frontalin+turpentine captured significantly more *D. frontalis* than traps baited with frontalin (in one elution device)+3:1, 1:1, 1:3, 0:1 turpentine:4-allylanisole (in one elution device) (x=87.6±21.0; P<0.0001, LSMeans, SAS Institute 1988). There was little difference between 25, 50 or 75% 4-allylanisole, but 100% 4- allylanisole caught significantly fewer *D. frontalis* than 25 and 50% (P<0.0347 and P<0.0439) (x=29.5±8.5; 22.2±4.9; 39.4±11.8; 15.0±6.0). The addition of 4-allylanisole in differing concentrations with turpentine did not impact *T. dubius* attraction to frontalin (x= 34.1±5.5; 33.5±7.8; 42.4±10.5; 28.1±5.8; 39.5±8.9).

Preliminary Field Trials:

Individual tree attributes and results of 30-day treatment of lightning struck pairs of pines were studied. The 4-allylanisole-treated member of each pair suffered fewer attacks than the untreated control. In two other noteworthy instances, large lightning struck loblolly pines in residential settings were treated within 48 hrs as described above. In one case the tree was protected even though a few pitch tubes were evident and the adjacent lightning struck tree was attacked by *D. frontalis* and removed by the owner. In the other case, a few pitch tubes were present at the time of treatment and after treatment was applied a few additional pitch tubes (apparently Ips sp.) were evident below the treated area; after the treatment was stopped at day 30, the tree was then attacked by Ips sp. and *D. frontalis* before the owner removed it.

This invention has been disclosed and described above with reference to both specific examples and generic concept. Alternatives will occur to those of skill in the art, particularly with respect to concentration, carrier and method of administration, without departing from the scope of the invention, save as limited by claims set forth below.

What is claimed is:

1. A method of repelling Scolytids from a surface subject to attack by said Scolytids, comprising applying an effective Scolytid repelling amount of 4-allylanisole to said surface.

2. A method of repelling Scolytids from a surface subject to attack by said Scolytids, comprising
   (i) impregnating solid supports with an effective Scolytid repelling amount of 4-allylanisole, and
   (ii) placing the impregnated solid supports proximate to a surface subject to attack by said Scolytids, whereby an effective Scolytid repelling amount of 4-allylanisole is eluted from said impregnated solid supports.

3. A method of protecting tree hosts from attack by scolytids comprising applying 4-allylanisole to trees subject to attack by scolytids in concentrations and amounts sufficient to repel said scolytids.

4. The method of claim 3, wherein said scolytids comprise insects in the family Scolytidae that attack coniferous hosts.

5. The method of claim 3, wherein said tree host comprises conifers.

6. The method of claim 3, wherein said tree host comprises pines.

7. The method of claim 3, wherein said tree host comprises firs and spruce.

* * * * *